(12) United States Patent
Bonte et al.

(10) Patent No.: US 6,193,975 B1
(45) Date of Patent: Feb. 27, 2001

(54) USE OF POTENTILLA ERECTA EXTRACT IN THE COSMETIC AND PHARMACEUTICAL FIELD

(75) Inventors: Frédéric Bonte; Marc Dumas, both of Orleans; Catherine Chaudagne, Vitry-Aux-Loges; Alain Meybeck, Courbevoie, all of (FR)

(73) Assignee: LVMH Recherche, Paris (FR)

( * ) Notice: Subject to any disclaimer, the term of this patent is extended or adjusted under 35 U.S.C. 154(b) by 0 days.

(21) Appl. No.: 09/297,679

(22) PCT Filed: Nov. 6, 1997

(86) PCT No.: PCT/FR97/01988

§ 371 Date: May 6, 1999

§ 102(e) Date: May 6, 1999

(87) PCT Pub. No.: WO98/19664

PCT Pub. Date: May 14, 1998

(30) Foreign Application Priority Data

Nov. 7, 1996 (FR) .................................................. 96 13585

(51) Int. Cl.$^7$ ..................................................... A61K 35/78

(52) U.S. Cl. ........................................................... 424/195.1

(58) Field of Search ........................................... 424/195.1

(56) References Cited

U.S. PATENT DOCUMENTS 3,856,941 * 12/1974 Turner .
4,014,995 * 3/1977 Juliano et al. .
4,933,177 * 6/1990 Grollier et al. .
5,248,503 * 9/1993 Emanuel-King .

FOREIGN PATENT DOCUMENTS 810 222 A1   3/1997 (EP) .
2 734 478   11/1996 (FR) .

OTHER PUBLICATIONS

Fuhrmann: "Pflanzenextrakte für kosmetische Präparate", Seifen–Öle–Fette–Wachse, vol. 115, No. 2, 1989, Augsburg, DE, pp. 38–40, XP000027104, *p. 38, paragraph "Adstringierende wirkung"*.
STN, Serveur de Bases de Données, XP002033781, Karlsruhe, de, Fichier Embase, AN=95338953, 1995.
Patent Abstracts of Japan, vol. 95, No. 006© & JP 07 061916 A (Sansho Seiyaku Co), 1995.
"Verwendung von Herbasol–Extrakten in der Kosmetik", SEIFE–Öle–Fette Wachse, vol. 107, No. 20, 1981, Augsburg, DE, pp. 623–625, XP002033780.
Database WPI, Week 8813, Derwent Publications LTD., London, GB, AN 88–086587, XP002033782, & HU 44 165 A (VADSZ), 1988.
Database WPI, Week 9139, Derwent Publications LTD., London, GB, AN 91–284717, XP002033783, & JP 03 188 008 A (Shiseido), 1991.
Internet Webpage: http://www.funet.fi/pub/sci/bio/life/plants/magnoliophyta/magnoliopsida/rosaceae/potentilla/index.html; p. 7 of printout Sep. 16, 1999.*
Webster's II; New Riverside University Dictionary. The Riverside Publishing Company, p. 1217, "tonic" definition, 1988.*

* cited by examiner

Primary Examiner—Francisco Prats
Assistant Examiner—Susan D. Coe
(74) Attorney, Agent, or Firm—Nath & Associates; Gary M. Nath

(57) ABSTRACT

The invention relates to the use of an extract of the plant *Potentilla erecta* in the field of cosmetics and pharmacy, especially in dermatology. The invention more particularly relates to any application in which it is sought to reinforce the dermo-epidermal junction or to improve hair condition, by the improvement of the synthesis of collagen VII by keratinocytes and/or fibroblasts. In particular, these applications concern toning of the skin, diminishing of wrinkles or hair care. The invention also relates to a novel method of culture of cells, in particular of human fibroblasts or keratinocytes, for promoting the formation of collagen VII.

27 Claims, No Drawings

USE OF POTENTILLA ERECTA EXTRACT IN THE COSMETIC AND PHARMACEUTICAL FIELD

The invention relates to a new use of an extract of *Potentilla erecta* in the field of cosmetics or pharmacy, especially in dermatology.

Tormentilla or *Potentilla erecta* Raeusch or *Potentilla tormentilla* Stokes or Neck is traditionally used in phytomedicine as an astringent, an anti-diarrhoea or as an anti-allergic. For this, see the work by Bisset "Herbal drugs and phytopharmaceuticals" CRC Press Ed, Boca Raton, USA, 1994, p. 499–501, as well as the book entitled: "A modem herbal" Penguin Handbooks, Harmards worth, England, 1980, p. 819–820.

Tormentilla is also a cultivated plant, in particular in central Russia in particular in Ural and is therefore easily accessible as has been described by Vasfilova E. S. and Ivanova G. A., Rastit. Resur 1989, 25, 67–73.

Bos et al., in the review Biological and Pharmaceutical Bulletin, 1996, 19, 146–148, have recently described an anti-lipoperoxidising and antielastasic activity of procyanidines extracted from tormentilla.

German patent DE 3911185 also describes the use of an extract of *Potentilla erecta* against bad breath.

Japanese patent application JP 01121221 of Daiso Co describes the use of an aqueous or organic extract of the same plant for treating diabetes, this extract having aldose reductase inhibiting properties.

A publication by Selemina L V., Zozulga R. N., Yakovleva T. N. in Rastit. Resur. 1973, 9, 409–414, describes the anti-inflammatory properties and those of an extract of the roots of tormentilla which improve the reinforcement of the walls of blood capillaries.

Other works have described the use of tannins of *Potentilla erecta* as anti-allergic agents and immunostimulants (Lund et al. Deutsche Apothekr Zeitung, 1985, 125, 105–108).

Furthermore, it is known that collagen of type VII, hereinafter designated as collagen VII, is the main constituent of the anchoring fibrils which are combined with the basal membrane, linking the epidermis to the dermis. It is synthesised by the keratinocytes of the basal layer of the epidermis, and in a lesser amount, by the fibroblasts of the dermis, as described by R.Burgeson in a publication entitled: "Type VII collagen, anchoring fibrils, and epidermolysis bullosa", J. Invest. Dermatol, (1993) 101,252–255. It will also be possible to refer to the publication of A. Koenig et al, in J. Invest. Dermatol. (1992) 99 808–812. As regards this, it will be noted that according to recent studies, topical applications of retinoic acid increased the number of anchoring fibrils on skins having undergone an actinic ageing (Woodley D. T. et al., J. Amer. Med. Assoc. (1990) 263, 3057–9). Retinoic acid, or tretinoin, is recognised as being one of the most efficient anti-wrinkle agents (L. H. Kligman, Cutis (1988) 41 (6) 419–20; J. J. Leyden et al, J. Am. Acad. Dermatol. (1989) 21 (3Pt 2) 638–44; J. H. Saurat, Horm. Res. (1995) 43 (1–3) 89–92).

According to the publication of Y. Q. Chen, A. Mauviel, J. Ryynanen, S. Sollberg, J. Uitto ("Type VII collagen gene expression by human skin fibroblasts and keratinocytes in culture: Influence of donor age and cytokine responses" J. Invest. Dermatol, (1994) 102, 205–209), certain manifestations of skin ageing, such as an increased skin fragility and a decrease in the capacities of repair of the epidermis, might be attributable to a reduction of the synthesis of collagen VII in aged subjects. It will be noted that the expression <<skin fragility>> in particular covers the appearance of sub-basal blisters.

Finally, it has been described by M. Akiyama et al. in J. Invest. Dermatol. (1995) 105 844–850, that collagen, collagen VII in particular, played an important role at the level of the human hair follicle, notably at the level of the basal membranes of the matrix (peripapillary zone) and at the level of the basal membrane of the bulge (bulge of the upper part of the bulb). These two areas contain cells having high mitotic potential, in particular keratinocytes giving rise to the hair stem. These authors indicated that the collagen VII present in the follicle is indispensable for the expression of this mitotic activity.

The authors of the present invention have now demonstrated, in an entirely surprising way, that an extract of *Potentilla erecta* has an effect upon the secretion of collagen VII by normal human keratinocytes.

This observation has led to the development of novel cosmetic or pharmaceutical compositions, notably dermatological compositions, which are more particularly useful in any application in which it is sought to stimulate the synthesis of collagen VII.

This property has proved to be particularly useful for the preparation of topical cosmetic or dermatological compositions. Such compositions in particular enable promoting the cohesion between the dermis and the epidermis in persons having a loosened or dull skin. The compositions have also proved to be useful for hair cares which are intended for improving hair condition. The compositions also enable treating pathologies which accompany a deficiency of the dermo-epidermal junction, such as epidermolysis bullosa.

Thus, according to one of its essential characteristics, the invention relates to the use of an extract of the plant *Potentilla erecta* as cosmetic agent intended for improving the cohesion between the dermis and the epidermis by reinforcing the dermo-epidermal junction, said agent being incorporated in a cosmetic composition comprising a cosmetically acceptable vehicle.

It has been clearly demonstrated that the extract incorporated in the composition acts by stimulating the formation of collagen VII, and this constitutes another essential characteristic of the invention.

Thus, the compositions of the invention prove to be particularly useful in any application in which it is sought to improve the cohesion between the dermis and the epidermis.

The composition will in particular be intended to obtain a toning of the skin, to prevent or to delay the appearance of signs of skin ageing, to delay the appearance of wrinkles or to decrease their depth, to improve hair condition.

It can be an anti-wrinkles product, a product intended for fighting against skin ageing and loosening of the skin or it can be a hair care lotion.

The cosmetic compositions of the invention prove to be particularly interesting for fighting against skin ageing, in particular against actinic ageing of the skin, i.e. ageing induced by radiation, solar radiation in particular, more particularly ultraviolet solar radiation.

Generally, the cosmetic compositions of the invention prove to be particularly useful as a product for toning the skin which is intended, in particular, for fighting against loose or dull skins.

According to another of its essential characteristics, the invention also relates to the use of an extract of the plant *Potentilla erecta* for preparing a pharmaceutical composition, notably a dermatological composition, intended for treating pathologies linked to a deficiency in the cohesion between the dermis and the epidermis, in particular those linked to a weakening of the dermo-epidermal junction.

The pharmaceutical compositions, notably dermatological compositions of the invention, will in particular find application in the treatment of manifestations or pathologies linked to an insufficiency in the formation of collagen VII.

Epidermolysis bullosa will in particular be cited as an example of such pathologies.

It will be possible for the dermatological compositions of the invention to be also advantageously used as a healing composition in the treatment of wounds, optionally as a supplement to local therapeutic treatments, in particular for improving the quality of the skin before and after healing.

It will be possible for various solvents to be used for obtaining an extract of the plant used in accordance with the present invention. However, water, a $C_1$ to $C_4$ alcohol, a $C_2$ to $C_6$ glycol, or any mixture of the solvents mentioned above will advantageously be selected, in particular an aqueous alcohol mixture or aqueous glycol mixture. Of course, the extraction solvent is selected such that it be liquid at ordinary temperature, i.e. 20–25° C.

Water will be the extraction solvent which is preferably used according to the invention.

It is more particularly preferred to use methanol or ethanol from the alcohols mentioned above. It is preferred to use ethylene glycol, propylene glycol or butylene glycol from the glycols. Butylene glycol will advantageously be selected.

The extract of the plant *Potentilla erecta* will advantageously be obtained from the rhizome of this plant in the two fields of cosmetic and pharmaceutical applications.

Thus, according to a particularly advantageous variant, an aqueous extract of the rhizome of *Potentilla erecta* will be used for the preparation of the compositions of the invention.

The cosmetic or pharmaceutical compositions, notably dermatological compositions of the invention, will advantageously contain 0.0001% to 5%, preferably between 0.01 and 0.5% by weight of said extract of *Potentilla erecta* with respect to the total weight of the composition.

It will be possible for the compositions of the invention to advantageously further comprise at least one substance which promotes the synthesis of the constituents of the extracellular matrix of the skin.

Vitamins, in particular vitamins from the A and C group and derivatives thereof such as esters, tocopherols, xanthines, in particular caffeine or theophylline, retinoids, in particular vitamin A acid, extracts of *centella asiatica*, asiatic acids, madecassic acids and glycosylated derivatives thereof such as asiaticoside or madecassoside, extracts of *Siegesbeckia orientalis*, extracts of *Commiphora mukul* and extracts of *Eriobotrya japonica* will be cited as examples of such substances.

Furthermore, the composition according to the invention can further contain at least one substance selected from the group constituted by aliphatic $C_3$–$C_{12}$ alpha-hydroxy-acids, in particular citric acid, malic acid and lactic acid, amino acids, in particular arginine, citrulline and threonine, ceramides, glycoceramides, phospholipids, slimming agents, in particular forskolin, extracts of Coleus, extracts of Tephrosia, anti-stretch mark agents, in particular extracts of horse chestnut and escine, agents which protect or which improve micro-circulation, in particular bioflavonoids of Ginkgo Biloba, and solar filters, in particular titanium oxides, Parsol MCX and filters of plant origin.

The extract of the plant *Potentilla erecta*, in the compositions of the invention which are more particularly intended for the treatment and the care of the hair, will advantageously be combined with at least one other active principle selected from the group constituted by anti-dandruff agents, such as extracts of *Arctium lappa*, chloroxylenol, resorcinol or zinc pyrithione, anti-seborrhoea agents such as a 5α-reductase inhibitor, in particular an extract of *Pygeum africanum*, and agents which stimulate blood microcirculation such as cepharanthine and methyl nicotinate.

Various forms of formulations can be prepared. One of the most used forms is a topical form which is adapted for application onto the cutaneous tissue. These suitable topical formulations include, without limitation, emulsions, creams, milks, balms, gels, lotions as well as treatment make-up compositions.

The invention, according to other aspects, also relates to a method of cosmetic treatment or pharmaceutical treatment, notably dermatological treatment, according to which it is sought to obtain an improvement of the junction between the dermis and the epidermis, by a reinforcement of the dermo-epidermal junction, or a stimulation of the synthesis of collagen VII.

This effect is obtained according to the invention by applying, onto the part of the body to be treated, a cosmetically, respectively pharmaceutically, effective amount of a cosmetically, respectively pharmaceutically effective extract of *Potentilla erecta*, said extract being incorporated in a composition comprising a cosmetically, respectively pharmaceutically acceptable excipient.

The method as defined above will particularly enable obtaining a toning of the skin, preventing or delaying the appearance of signs of skin ageing, delaying the appearance of wrinkles or decreasing their depth.

The compositions used for implementing this method are those defined above.

Finally, according to its last aspect, the invention also relates to a method of treatment of cells in culture, in particular of human keratinocytes or of human fibroblasts according to which an effective concentration of an extract of the plant *Potentilla erecta* is introduced to obtain a stimulation of the synthesis of collagen VII.

According to preferred implementation variant of this method, the above-mentioned extract is introduced at a concentration of between 0.0001% and 1% by weight with respect to the total weight of the culture medium.

Other aims, characteristics, and advantages of the invention appear clearly to the person skilled in the art from the following explanatory description which is made with reference to several examples of embodiments which are given simply as an illustration and which in no way limit the scope of the invention. In the Examples which follow, the percentages are given by weight, unless indicated otherwise.

EXAMPLES

Example 1

Preparation of a Methanol Extract of Rhizomes of *Potentilla erecta*

One part by weight of the plant rhizomes is extracted thrice in a row with 10 parts of methanol, under reflux, each time for 30 minutes. All the extracts are combined after filtration.

The extract is then concentrated up to the total removal of the solvent. A product is thus recovered in the form of a dry extract.

Example 2

Preparation of an Extract of Rhizomes of *Potentilla erecta* by Aqueous Extraction 50 g of the plant rhizomes, finely ground, are used, and an extraction is made with 500 ml of boiling water for 30 minutes. After filtering on a grid of porosity 0.45 μm, the solid residue is extracted twice in a row under the same conditions as the first extraction, with 500 ml of water. All the aqueous extracts were then combined and then lyophilised. A dry extract is thus obtained in the form of a powder.

Example 3

Demonstration of the Stimulation of the Synthesis of Collagen VII by an Aqueous Extract of Rhizomes of *Potentilla erecta*

The above test was carried out on the aqueous extract in the form of a lyophilised powder, hereinafter referred to as AE, obtained according to the method described in Example 2.

The tests were carried out blind.

1—Protocol of the Test a) Source of the Keratinocytes

Cultures of normal human keratinocytes (NHK) are established from a surgical sample of healthy skin. In the present study, the tests are carried out on a cell strain originating from a lifting of a 58-year old Caucasian woman.

b) Culture Conditions:

The keratinocytes are kept in a complete SFM (Serum Free Medium) (designated as SFMc, GIBCO). The cells were under cultivated once from the first culture (i.e. one passage, designated P1).

c) Treatment Conditions:

The sowing of the cells is carried out in a 96-well culture plate at the rate of 30,000 NHK per well in SFMc. After 24 hours of incubation necessary for a good adherence of the cells, the medium is replaced by an SFMc diluted to 2%, limiting the proliferation of the keratinocytes. The mother solutions of product obtained according to Example 2 (referred to as AE in Table 1) are prepared extemporaneously in DMSO at concentrations of 1–2.5–5 mg/ml and introduced into the study medium at 0.1% V/V final (i.e. the concentrations tested: 1–2.5–5 μg/ml). The control received the excipient of the product, i.e. 0.1% V/V of DMSO. Six cultures were prepared for each of the three concentrations and for the control test. The viability test XTT, as well as the microscopic observation of the cells, did not reveal any cytotoxic effects of the product at concentrations lower than 10 μg/ml. (XTT kit, BOEHRINGER, Ref. 1465015).

The cells are placed in contact with the treatment medium for 72 hours, the time required for an optimal synthesis of collagen VII according to a prior kinetic study.

The incubation supernatants are taken with a view to determining the collagen VII secreted. A determination of the proteins is carried out on the cell mat which remains in the wells (BCA method, SIGMA), with the aim of establishing a relationship between the amounts of collagen VII secreted and the levels of cell proteins.

d) ELISA Determination of the Collagen VII:

The collagen VII determination protocol by an ELISA method was adapted from that used for determination of collagen I (M. DUMAS, C. CHAUDAGNE, F. BONTE, A. MEYBECK: "In vitro biosynthesis of type I and III collagens by human dermal fibroblasts from donors of increasing age", Mechanisms of Ageing and Development, 73 (1994) 179–187).

The following modifications were made:

$1^{st}$ antibody: Human Type VII monoclonal mouse anti-collagen antibody, isotype IgG1 (Life Technologies, Ref. 12073–011, Lot FB2b01).

$2^{nd}$ antibody: Mouse total anti-IgG goat antibodies, coupled to alkaline phosphatase (Interchim, Ref. 115-056-062, Lot 26793).

e) Expression of the Results and Statistical Interpretation:

In the absence of commercially available human type VII collagen for establishing a standard range, the results of the secretion of collagen VII by the keratinocytes are expressed in units of optical density, to which the determination control test is subtracted (designated O.D.—Blank). These values are brought back to the levels of cell proteins of the corresponding well (for 72 hours of incubation).

The activity of the product is evaluated by the percentage of stimulation:

[(Collagen VII of the treated NHKs–Collagen VII of the control NHKs)/Collagen VII of the control NHKs]×100.

The results obtained on the treated cultures (n=6) and control cultures (n=6) are compared by the non-paired Student test, the significance threshold retained being $p<0.05$.

The activity of product A on the collagen VII was the subject of a confirmation on the same NHK strain.

Results—Conclusion

The results are given in Table 1 below, from the average of the measurements on the various cultures:

TABLE 1

COLLAGEN VII IN RELATION TO THE LEVEL OF PROTEINS

| Products | Concentrations | O.D. - Blank collagen VII/ 100 μg proteins/72 h | p (test t) with respect to the control | Significance |
| --- | --- | --- | --- | --- |
| Control SFMc 2% + DMSO 0.1% | — | 1.099 +/– 0.165 | | |
| AE | 2.5 μg/ml | 1.557 +/– 0.238 | 0.004 | S (+42%) |
| AE | 10 μg/ml | 1.490 +/– 0.204 | 0.004 | S (+36%) |

N.S.: non significant
S: significant ($p < 0.05$)

The results appearing in Table 1 show a significant stimulation of collagen VII by the aqueous extract of *Potentilla erecta* with concentrations of 2.5 and 10 μg/ml.

Thus, it appears clearly that the extracts of *Potentilla erecta* stimulate the formation of collagen VII. This protein notably being the main constituent of anchoring fibrils, these extracts can therefore advantageously be used as an agent for reinforcing the dermo-epidermal junction, and for thus improving the cohesion between the dermis and the epidermis.

Furthermore, it is known notably from the publication by M. Akiyama cited above, that collagen VII is indispensable for the expression of the mitotic activity of the keratinocytes of the human hair follicles, from where the interest comes of the extracts of *Potentilla erecta* for improving hair condition.

Example 4

Demonstration of the Stimulation of the Synthesis of Collagen VII by a Methanol Extract of Rhizomes of *Potentilla erecta*

This demonstration is carried out with a methanol extract, hereinafter designated as <<ME>>, obtained according to the method described in Example 1.

The experimental protocol used is exactly the same as that described in the preceding Example in relation to the test with the aqueous extract, except that the normal human keratinocytes (NHK) used this time originate from a lifting on a 56-year old Caucasian woman.

The results obtained are given in Table II below, from the average of the measurements on the various cultures.

TABLE II

COLLAGEN VII COMPARED TO THE LEVEL OF PROTEINS

| Products | Concentrations | O.D. - Blank collagen VII/ 100 µg proteins/72 h | p (test t) with respect to the control | Significance |
|---|---|---|---|---|
| Control SFMc 2% + DMSO 0.1% | — | 1.096 +/− 0.146 | | |
| ME | 1 µg/ml | 1.155 +/− 0.069 | 0.3987 | N.S. (+5%) |
| ME | 2.5 µg/ml | 1.387 +/− 0.186 | 0.0138 | S (+26%) |
| ME | 5 µg/ml | 1.422 +/− 0.199 | 0.0100 | S (+30%) |

N.S.: non significant
S: significant (p < 0.05)

The results appearing in Table II above show that the methanol extracts according to the invention possess, from a certain concentration, a very significant effect of stimulation of the formation of collagen VII.

These results confirm the conclusions of the test relating to the aqueous extracts of the preceding Example, namely that the extracts of the plant *Potentilla erecta* have great importance firstly in the reinforcement of the cutaneous dermo-epidermal junction, and secondly, in the improvement of hair condition.

Example 5

Cosmetic Care Composition Against Skin Loosening

Methanol extract of rhizomes of Tormentilla according to Example 1: 0.2 g
Extract of *Centella asiatica*: 0.1 g
Vitamin C: 0.1 g
emulsified excipient in the form of an oil-in-water emulsion, perfume and preservative: qsp 100 g This composition fights against the loosening of the skin, and restores its firmness. The composition can advantageously be used by cures of 3 weeks in applications on the areas of the body to be treated on which the skin has loosened.

Example 6

Gelified Dermatological Preparation for the Treatment of Epidermnolysis Bullosa

Methanol extract of rhizomes of Tormentilla, according to example 1: 0.5 g
carbopol 980®: 1.5 g
ethanol: 2.0 g
aqueous excipient: qsp 100 g It will be necessary for this gelified preparation to be applied locally onto the areas to be treated in case of epidermolysis, 3 times daily for at least 15 days.

Example 7

<<Anti-age>> Emulsion

Methanol extract of rhizomes of Tormentilla according to example 1: 0.2 g
Vitamin A palmitate: 0.08 g
Magnesium ascorbic phosphate: 2.0 g
Wheat ceramides: 0.3 g
Perfumed fluid emulsified excipient: qsp 100 g This emulsion can be used on the areas of the body to be treated, on the face in particular, preferably each evening. This emulsion contributes in delaying the appearance of signs of ageing of the skin such as wrinkles or skin loosening. After a daily treatment of about 6 months, the skin becomes smoother, more supple and fixmer. It regains its brilliance.

Example 8

Treatment Tint Base

Aqueous extract of rhizomes of *Potentilla erecta* according to example 2: 0.05 g
Nylon SP500 powder: 2.0 g
Serine: 0.1 g
Threonine: 0.1 g
Magnesium ascorbic phosphate: 1.2 g
Madecassoside: 0.1 g
Excipients with pigments and preservatives: qsp 100 g The regular use of this tint base will contribute in keeping the skin in good condition and in fighting against skin ageing.

Example 9

Make-up Powder Compact

Methanol extract of *Potentilla erecta* according to example 1: 0.08 g
Orgasol 2002 HD (Nylon) powder: 3.0 g
Lactic acid: 0.2 g
Excipient: qsp 100 g This powder compact enables, whilst being a skin make-up, delaying its ageing.

Example 10

Occlusive Film for the Treatment of Wrinkles

Vitamin A palmitate: 0.01 g
Aqueous extract of *Potentilla erecta* according to example 2: 0.05 g
Magnesium ascorbic phosphate salt: 2.00 g
Wheat proteins: 10.00 g
Glycerol: 1.00 g
Excipients: qsp 100.00 g This composition applied onto the skin forms, after evaporation of the water, a film of occlusive character, also designated in the professional language by the term <<mask>> or even by <<patch>>. Preferably, this composition is applied in the evening onto the areas of the skin to be treated, for example above the cheekbones on the area of the <<goose foot>> wrinkles. The treatment film thus formed is left in place for several hours. After 15 days of daily treatment, the small wrinkles very clearly become smoothed out. The treatment is generally recommended by cures for 30 days, 3 to 4 times per annum.

Example 11

Hair Lotion for Improving Hair Condition and for Fighting Against the Formation of Dandruff Methanol extract of *Potentilla erecta* according to example 1: 0.1 g Chloroxylenol: 0.05 g
Cepharantine: 0.01 g
Perfumed alcohol excipient: qsp 100.00 g The lotion is used by applications morning and night onto the scalp, followed by light massage. After 8 to 15 days of treatment, the hair regains its brilliance and its suppleness, and the itching disappears. The cures recommended are of 30 days, spaced out by 2 to 4 months according to the significance of the hair problem to be treated.

What is claimed is:

1. A method of treatment of the human body selected from the group consisting of a method for improving the junction between the dermis and the epidermis by reinforcement of the dermo-epidermal junction and a method for stimulating the formation of collagen VII, which comprises the topical application to an external area of the human body of a cosmetical or pharmaceutical composition comprising at least one active agent consisting essentially of a cosmetically or phamaceutically effective amount of an extract of the plant *Potentilla erecta*, wherein said extract is obtained by extraction with the aid of a solvent selected from the group consisting of water, $C_1$–$C_4$ alcohols, $C_2$–$C_6$ glycols, and mixtures thereof.

2. A method of cosmetic care of the human body for firming the skin, comprising the topical application to a skin area in need thereof of the human body of a cosmetical composition comprising at least one cosmeticsally active agent for firming the skin, said active agent for firming the skin consisting essentially of a cosmetically effective amount of an extract of the plant *Potentilla erecta*, wherein said extract being obtained by extraction with the aid of a solvent selected from the group consisting of water, $C_1$–$C_4$ alcohols, $C_2$–$C_6$ glycols, and mixtures thereof.

3. A method of cosmetic care of the human body for slowing the appearance of the signs of the skin ageing comprising the topical application to a skin area in need thereof of the human body of a cosmetical composition comprising at least one cosmetically active agent against the skin ageing, said active agent against the skin ageing consisting essentially of a cosmetically effective amount of an extract of the plan *Potentilla erecta*, said extract obtained by extraction with the aid of a solvent selected from the group consisting of water, $C_1$–$C_4$ alcohols, $C_2$–$C_6$ glycols, and mixtures thereof.

4. A method of cosmetic care for delaying the appearance of wrinkles or to increase their depth, comprising the topical application to a skin area in need thereof of the human body of a cosmetical composition comprising at least one cosmetically active agent against the skin wrinkles, said active agent against the skin wrinkles consisting essentially of a cosmetically effective amount of an extract of the plant *Potentilla erecta*, said extract being obtained by extraction with the aid of a solvent selected from the group consisting of water, $C_1$–$C_4$ alcohols, $C_2$–$C_6$ glycols, and mixtures thereof.

5. A method of cosmetic care for fighting against actinic ageing of the skin, due to solar radiation comprising the topical application to a skin area in need thereof of the human body of a cosmetical composition comprising at least one cosmetically active agent against the skin actinic ageing, said active agent against the skin actinic ageing consisting essentially of a cosmetically effective amount of an extract of the plant *Potentilla erecta*, said extract being obtained by extraction with the aid of a solvent selected from the group consisting of water, $C_1$–$C_4$ alcohols, $C_2$–$C_6$ glycols, and mixtures thereof.

6. A method of cosmetic care for improving hair condition comprising the topical application to a skin area in need thereof of the human body of a cosmetical composition comprising at least one cosmetically active agent acting on hair, said hair active agent consisting essentially of a cosmetically effective amount of an extract of the plant *Potentilla erecta*, said extract being obtained by extraction with the aid of a solvent selected from the group consisting of water, $C_1$–$C_4$ alcohols, $C_2$–$C_6$ glycols, and mixtures thereof.

7. A method according to claim 1, wherein said solvent is water.

8. A method according to claim 1, wherein said solvent is methanol or ethanol.

9. A method according to claim 1, wherein said solvent is selected from the group constituted by ethylene glycol, propylene glycol and butylene glycol.

10. A method according to claim 9, wherein said extract is obtained by extraction with butylene glycol.

11. A method according to claim 1, wherein said extract is obtained from the plant rhizomes.

12. A method according to claim 1, wherein said composition contains 0.0001% to 5% by weight of said extract with respect to the total weight of said composition.

13. A method according to claim 1, wherein said composition further contains at least one substance which promotes the synthesis of the extracellular matrix of the skin.

14. A method according to claim 13, wherein said substance is selected from the group constituted by vitamins, extracts of *centella asiatica*, asiatic acids, madecassic acids and glycosylated derivatives thereof, extracts of *Siegesbeckia orientalis*, extracts of *Commiphora mukul* and extracts of *Eriobotrya japonica*.

15. A method according to claim 1, wherein said composition further contains at least one substance selected from the group consisting of aliphatic $C_3$–$C_{12}$ alpha-hydroxyacids, amino acids, ceramides, glycocermides, phospholipids, slimming agents, extracts of Colcus, extracts of Tephrosia, anti-stretch mark agents, agents which protect or which improve microcirculation, and solar filters.

16. A method according to claim 1, wherein said composition further contains at least one other active principle selected from the group consisting of anti-dandruff agents, anti-seborrhoea agents and agents which stimulate blood microcirculation.

17. A method according to claim 2, wherein said solvent is selected from the group consisting of water, methanol, ethanol, and mixtures thereof.

18. A method according to claim 3, wherein said solvent is selected from the group consisting of water, methanol, ethanol, and mixtures thereof.

19. A method according to claim 4, wherein said solvent is selected from the group consisting of water, methanol, ethanol, and mixtures thereof.

20. A method according to claim 5, wherein said solvent is selected from the group consisting of water, methanol, ethanol, and mixtures thereof.

21. A method according to claim 6, wherein said solvent is selected from the group consisting of water, methanol, ethanol, and mixtures thereof.

22. A method of treatment of the human body selected from the group consisting of a method for improving the junction between the dermis and the epidermis by a reinforcement of the dermo-epidermal junction, and a method for stimulating the formation of collagen VII, which comprises the topical application to an external area of the human body of a cosmetical or pharmaceutical composition comprising at least one active agent consisting essentially of a cosmetically or pharmaceutically effective amount of an extract of the plant *Potentilla erecta*, wherein said extract is obtained by extraction with the aid of a solvent selected from the group consisting of water, $C_1$–$C_4$ alcohols, $C_2$–$C_6$ glycols, and mixtures thereof, under the proviso that said *Potentilla erecta* extract is not combined with a kojic acid component selected from the group consisting of kojic acid, a kojic acid salt, and a kojic acid ester.

23. A method of cosmetic care for improving the junction between the dermis and the epidermis by the reinforcement of the dermo-epidermal junction, comprising the topical application to an external area of the human body of a cosmetical or pharmaceutical composition comprising as sole agent for improving the junction between the dermis and the epidermis, an effective amount of an extract of the plant *Potentilla erecta*, said extract being obtained by extraction with the aid of a solvent selected from the group consisting of water, $C_1$–$C_4$ alcohols, $C_2$–$C_6$ glycols, and mixtures thereof.

24. The method of claim 23, wherein the concentration of said extract of *Potentilla erecta* is between 0.0001% and 5% by weight with respect to the total weight of the composition.

25. The method of claim 24, wherein the concentration of said extract of *Potentilla erecta* is between 0.01% and 0.5% by weight with respect to the total weight of the composition.

26. The method of claim 23, wherein said extract is a methanol extract of the rhizome of *Potentilla erecta*.

27. The method of claim 23, wherein said extract of *Potentilla erecta* is an aqueous extract of the rhizome of *Potentilla erecta*.

* * * * *

UNITED STATES PATENT AND TRADEMARK OFFICE
CERTIFICATE OF CORRECTION

PATENT NO. : 6,193,975 B1
DATED : February 27, 2001
INVENTOR(S) : Bonte et al.

It is certified that error appears in the above-identified patent and that said Letters Patent is hereby corrected as shown below:

Column 9,
Line 45, please delete "increase" and replace with -- decrease --.

Signed and Sealed this

First Day of November, 2005

JON W. DUDAS
*Director of the United States Patent and Trademark Office*